United States Patent [19]

Menzies et al.

[11] Patent Number: 4,509,130
[45] Date of Patent: Apr. 2, 1985

[54] DIGITAL CONTROL OF DIODE LASER FOR ATMOSPHERIC SPECTROSCOPY

[75] Inventors: Robert T. Menzies, Pasadena; Charles W. Rutledge, Temple City, both of Calif.

[73] Assignee: The United States of America as represented by the Administrator of the National Aeronautics and Space Administration, Washington, D.C.

[21] Appl. No.: 384,547

[22] Filed: Jun. 3, 1982

[51] Int. Cl.³ .................... G01N 21/25; G01N 21/29
[52] U.S. Cl. ................................. 364/556; 250/339
[58] Field of Search .................... 364/496–498, 364/550, 556; 356/303, 319, 320; 250/339, 345, 354.1; 372/41, 20

[56] References Cited

U.S. PATENT DOCUMENTS

| | | | |
|---|---|---|---|
| 3,805,074 | 4/1974 | McCormack | 250/339 |
| 3,829,694 | 8/1974 | Goto | 250/339 |
| 3,863,177 | 1/1975 | Daman et al. | 372/41 |
| 4,410,273 | 10/1983 | Mantz et al. | 250/339 |
| 4,410,992 | 10/1983 | Javan | 372/20 |
| 4,425,503 | 1/1984 | Watkins et al. | 250/345 |

OTHER PUBLICATIONS

Argonne National Laboratory's, "Gamma Ray Spectrometer", 9/64.

Primary Examiner—James D. Thomas
Assistant Examiner—Dale M. Shaw
Attorney, Agent, or Firm—Paul F. McCaul; John R. Manning; Thomas H. Jones

[57] ABSTRACT

A system for remote absorption spectroscopy of trace species using a diode laser (14) tunable over a useful spectral region of 50 to 200 cm$^{-1}$ by control of diode laser temperature over range from 15° K. to 100° K., and tunable over a smaller region of typically 0.1 to 10 cm$^{-1}$ by control of the diode laser current over a range from 0 to 2 amps. Diode laser temperature and current set points are transmitted to the instrument in digital form and stored in memory (32) for retrieval under control of a microprocessor (28) during measurements. The laser diode current is determined by a digital-to-analog converter (62) through a field-effect transistor ($Q_1$) for a high degree of ambient temperature stability, while the laser diode temperature is determined by set points entered into a digital-to-analog converter (64) under control of the microprocessor. Temperature of the laser diode is sensed by a sensor diode (18) to provide negative feedback to the temperature control circuit that responds to the temperature control digital-to-analog converter (64).

9 Claims, 3 Drawing Figures

DIGITAL CONTROL OF DIODE LASER FOR ATMOSPHERIC SPECTROSCOPY

ORIGIN OF INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

This invention relates to atmospheric absorption spectroscopy, and more particularly to digital control of a tunable diode laser (TDL) in the atmosphere from a ground station.

Spectrometers utilizing diode lasers have been made available for analytical use in laboratories. Typically, they provide spectral resolution over a limited range in the 330 to 3600 $cm^{-1}$ infrared spectral region. These spectrometers are useful in a variety of high resolution experiments, which include low level trace species detection.

The measurement of trace species can also be accomplished in the atmosphere using a TDL instrument, provided the diode laser can be remotely tuned through the desired wavelength region for interaction with specific atmospheric species. The potential of an instrument containing several TDLs, each of which can be separately tuned to simultaneously measure several reactive gaseous species in the stratosphere, makes it particularly attractive for stratospheric photochemistry. The application demands stable output wavelengths and the ability to tune the lasers with high precision, due to the fact that, at the low stratospheric pressures, the absorption lines are very narrow.

An instrument which utilizes high resolution spectroscopy with TDLs must have such accurate frequency control and high stability requirements as to present a challenge to the designer, even in a fairly well controlled laboratory environment. (This is because the output wavelength of a TDL varies as a function of temperature over a significant region). With a required temperature set-point resolution on the order of milli-Kelvins ($10^{-3}$ K.), and stability requirements of a fraction of a milli-Kelvin, factors usually ignored become quite noticeable.

In a commercial TDL temperature controller designed for laboratory use, a refrigeration unit utilizes pressurized helium gas in a closed-cycle cooler, referred to as the cold head, to maintain the cryogenic temperatures of the TDL's environment. Silicon diode sensors sense the temperature of the TDL heat sink, referred to as the cold finger, to provide a feedback signal for precise temperature control of the TDLs using an electrical heating element to stabilize the cold finger temperature.

The TDLs are tuned within a particular wavelength region by controlling the operating temperature at a set point, typically between 15° K. and 100° K., and by controlled changes in the currents passed through the TDLs. Temperature tuning rates are typically 4 $cm^{-1}/°K$. Current tuning rates are typically between $2-5 \times 10^{-3}$ $cm^{-1}$ per milliamp. In practice, a stable TDL current control voltage source is divided down to the set-point level through a series of high quality potentiometers. The potentiometers are manually adjusted to the desired setting by the user. A TDL temperature controller having its own voltage source divided down to a temperature set through a series of high quality potentiometers then stabilizes the temperature. A commercial instrument based on these principles has been used extensively in laboratories with good results, but it is not suitable for certain environments where extreme stability and remote control are required.

The instrument for atmospheric studies must be self-contained, and linked to the user via an RF link. Therefore all settings, adjustments, and data must be communicated through this RF link. Since the ambient temperature and pressure change considerably during flight, thermal stability of the control and monitoring system is very important.

SUMMARY OF THE INVENTION

In an exemplary embodiment of the invention, at least one tunable diode laser (TDL) is carried into the atmosphere, such as by a balloon, for measurement of trace species, although in practice the TDL may be simply placed at any remote location. The TDL temperature and current are both controlled through an RF link for tuning through a predetermined range. The TDL operating temperature is set for operation over a predetermined range, and the TDL wavelength is tuned over this range by controlling the current passing through the TDL. Measurements are then telemetered from the remote location via the RF link.

To make this remote tuning possible, separate digital-to-analog converters (DACs) are provided for the temperature and current set points. The output of the temperature control DAC regulates the operating temperature of the TDL for the particular wavelength region or absorption line desired. In practice, the output of the temperature control DAC is applied to the input of an operational amplifier which controls current through a heater that is thermally coupled to both the TDL and a temperature sensor. The temperature sensor provides a negative feedback signal to the operational amplifier to stabilize the TDL temperature. Fine tuning the TDL within that region or absorption line is then accomplished by digital control of current using another DAC, the output of which is applied to a field-effect transistor (FET) through a noninverting input terminal of an operational amplifier, while a current sensor feedback voltage is applied to the FET through an inverting input to the operational amplifier.

The novel features that are considered characteristic of this invention are set forth with particularity in the appended claims. The invention will best be understood from the following description when read in connection with the accompanying drawings.

DESCRIPTION OF PREFERRED EMBODIMENTS

Figure 1:
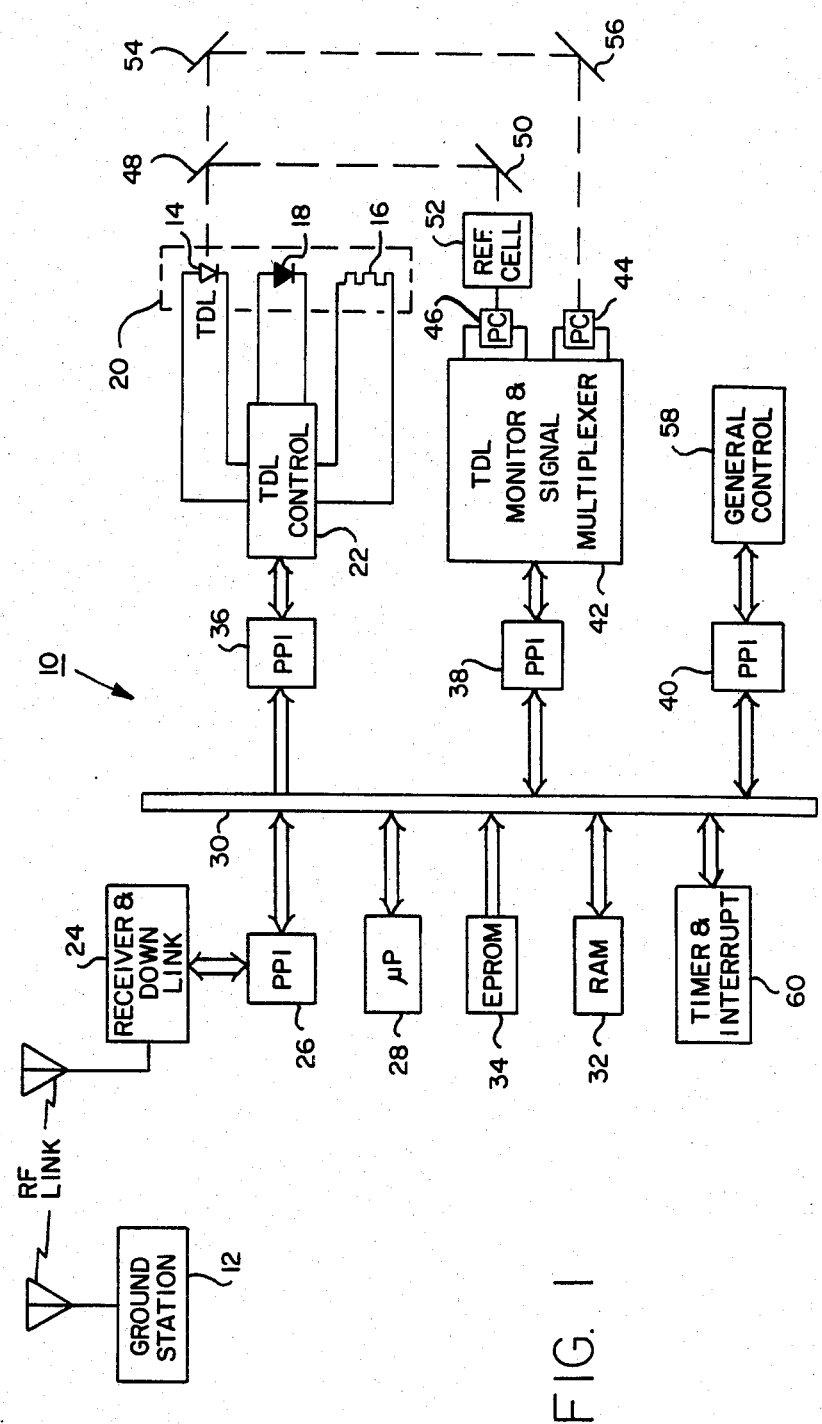
FIG. 1 is a block diagram of a system embodying the present invention for measurement of trace species in the atmosphere using a tunable diode laser (TDL) with control of TDL bulk temperature and current from a ground station via an RF link.

Referring now to FIG. 1, an instrument 10 borne into the stratosphere by a balloon for in-situ measurement of trace species, is linked to a ground station 12 by an RF link. The instrument utilizes a Pb-salt or other diode laser (TDL) 14 designed for operation in a particular region of the 330 cm$^{-1}$ to 3600 cm$^{-1}$ infrared with resolution of 0.003 cm$^{-1}$, and typically covering a spectral region of from 50 cm$^{-1}$ to 200 cm$^{-1}$. A spectroscopy instrument with those specifications is commercially available with interchangeable Pb-salt diode lasers as a Model LS-3 Laser Source Spectrometer from Laser Analytics, Inc., a division of Spectra-Physics, Inc. However, that commercial instrument was designed for use under reasonably controlled conditions in a laboratory where the user has direct access to thumb-wheel potentiometers for establishing a TDL current set point within the 50 to 200 cm$^{-1}$ range of a given TDL, and tuning within that range by changes in operating temperature between 15° K. and 100° K. Typically, one degree K. affects the laser output 4 cm$^{-1}$.

The temperature and current set points are achieved in that commercial instrument using a voltage source divided down through a series of high quality potentiometers, and temperature stability is achieved by sensing the TDL temperature to provide suitable negative feedback to a temperature control input voltage. The sensor is a diode mounted in thermal contact with the TDL and heater. Biasing the sensor diode is achieved with a floating constant current source connected in parallel therewith and the set-point voltage is applied to the diode in parallel with its floating current source. An operational amplifier that couples the sensor diode and its constant current source to the heater amplifies only the difference between the set-point voltage and the voltage provided by the sensor. This difference (error signal) corrects the temperature to the set point. However, as noted hereinbefore, such a commercial instrument is not suitable for remote spectroscopy studies such as stratospheric studies and other environmental applications, which demand greater stability and the ability to remotely tune the lasers by temperature control with high precision. This is due to the fact that at the low stratospheric pressures the absorption lines are very narrow. Also the temperature environment of the instrument is not as well controlled as in a standard laboratory. Moreover, such studies require remote control of the instrument.

The present invention utilizes a heater 16 and a silicon diode sensor 18 thermally coupled to the TDL in much the same way as in the prior art, but with improved control. The thermal coupling is by a finger of a cold head cryogenically cooled. The cold finger is indicated in FIG. 1 by a dotted line block 20. Improvements that will achieve a more stable TDL control are contained within a unit 22, as will be described more fully hereinafter with reference to FIG. 2.

The TDL control unit receives set points for control of current through the TDL 14 and the cold finger temperature to be maintained through the closed loop of the heater 16 and sensor 18. These set points are transmitted from the ground station 12 in the form of coded pulses, and received by the instrument 10 through a receiver and down link unit 24. A programmable peripheral interface (PPI) 26 couples the receiver and down link 24 to a microprocessor ($\mu$p) 28 through a bus 30.

The microprocessor 28 directs the received set points to a random access memory (RAM) 32 where they are stored until needed in the programmed control of absorption measurements at different wavelengths determined by these set points. The microprocessor also receives and decodes commands from the ground station.

Initial set points, and other parameters, are stored in an electronically programmable read only memory (EPROM), and loaded into the RAM by the microprocessor at the appropriate time with a single command. Changes in these set points, and parameters, are accomplished in the RAM under commands from the ground station. The commands instruct the microprocessor to output the destination address and data (set points) on the bus. Programmable peripheral interfaces 36, 38 and 40 couple the peripheral units, such as the TDL control unit 22, to the bus 30. Each programmable peripheral interface may be comprised of a general purpose programmable input-output integrated circuit designed for use with the microprocessor, such as in Intel 8255A programmable peripheral interface designed for use with an Intel 8085 microprocessor.

Every programmable peripheral interface provides a buffer for a bidirectional data bus and read/write control logic. In the case of the PPI 36, it simply provides a buffer for the set points. In the case of the PPI 38, it provides an input and output buffer for a TDL monitor 42, which includes a multiplexer for monitoring more than one parameter as well as for reading a signal photoconductor 44 and a reference photoconductor 46. Infrared radiation of the programmed wavelength is emitted by the TDL 14 and divided by a beamsplitter 48 into two beams. One beam is diverted by a mirror 50 through a reference cell 52, and the other is directed by mirrors 54 and 56 to the signal detector 44. (The path between the mirrors 54 and 56 passes through the atmosphere for measurement of trace species, whereas the path between the beam splitter 48 and the mirror 50 does not in order to provide a reference measurement.) And finally, the PPI 40 provides an input and output buffer for a general control unit 58 included in this exemplary system for controlling and monitoring the state of different units, such as to turn on and off the various power supply voltages required for the different units.

A programmable interval timer and interrupt controller 60 are used by the microprocessor to time events, such as intervals for measurements, and to permit the microprocessor to be interrupted by the timer, as well as by all other peripheral units connected to it through the bus 30, including the receiver and down link unit 24 which, with its PPI 26, is considered by the microprocessor as just any other peripheral unit coupled to it by the bus 30.

Figure 2:
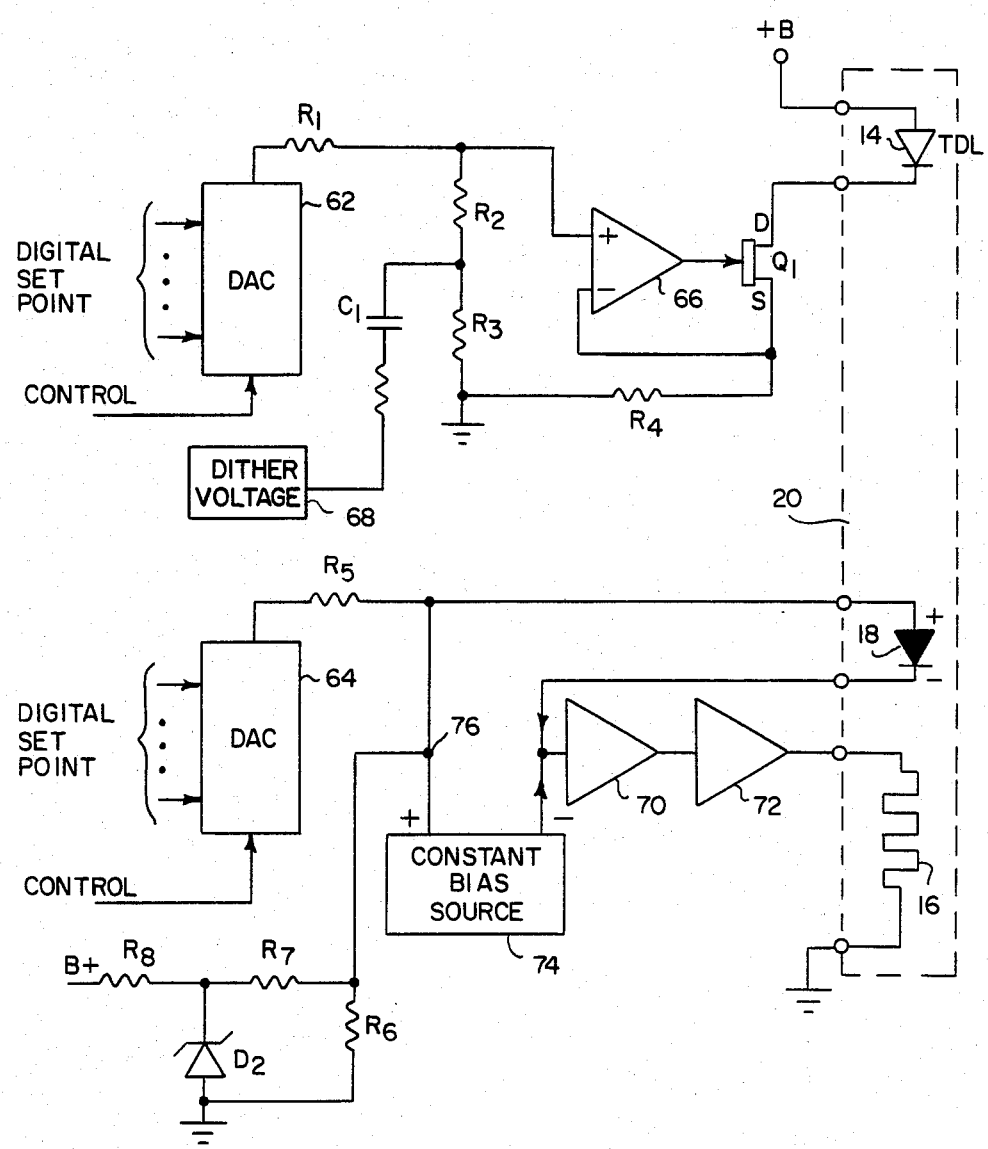
FIG. 2 is a circuit diagram for TDL current and temperature control in the system of FIG. 1.

Referring now to FIG. 2, the TDL control unit 22 is comprised of two digital-to-analog converters 62 and 64 for receiving the TDL current and temperature set points in digital form under control of the microprocessor 28 (FIG. 1), which in turn may be commanded by the ground station 12 via the RF link. The current control DAC 62 converts the digital wavelength ($\lambda$) set point to a voltage with a resolution of one part in $2^N$, where N is the number of binary digits of the digital input, such as 16. The output voltage of the DAC 62 controls current through the TDL 14 by control of the gate voltage of a field-effect transistor $Q_1$ through an operational amplifier 66. The output of the DAC 62 is coupled to the operational amplifier 66 by a voltage dividing network comprised of resistor $R_1$, $R_2$ and $R_3$. A dither voltage signal from a source 68 is added at the junction between the resistors $R_2$ and $R_3$ through a coupling capacitor $C_1$.

The source electrode of the FET is connected to circuit ground by a resistor $R_4$. It develops a voltage proportional to the drain-to-source current ($I_{DS}$). If this current should increase, thus changing the wavelength of the radiation of the TDL, an increase in voltage across the resistor $R_4$ is sensed and fed back to the inverting input terminal of the operational amplifier 66. This increase in the feedback signal increases the output of the operational amplifier 66, which in turn decreases the drain-to-source current. In that way, the current through the TDL is stabilized at a level corresponding to the digital set point stored in the DAC register.

the DAC 62 is a 16 bit Analog Devices Model 1136L 6-1-1-1 card assembly with an input register, a module for removing any short unwanted high amplitude transients, and a low drift output amplifier. The DAC output ranges from 0 to 10 volts and is divided down to a range from 0 to 2.097 volts by the resistors $R_1$, $R_2$ and $R_3$. The current controller uses this voltage as a reference at the noninverting input of the amplifier 66 for the TDL current, which is typically adjusted for a 0 to 1.048 amp range, with the capability of 0 to 2.097 amps if desired. The current sense resistor $R_4$ for the current control loop is a 1 ohm 50 watt RH style resistor. The voltage across this sense resistor is fed back differentially to the operational amplifier 66. For derivative spectroscopy, a programmable 2.048 KHz dither current is injected into the current source control by the dither signal from the source 68, thus modulating with the wavelengths of the TDL output. The signal at the diode sensor 44 (FIG. 1) can then be synchronously detected.

The output wavelength of the TDL may be tuned over a range changing its operating temperature between 28° K. and 45° K. This more limited temperature range compared with a general TDL operating range from 15° K.–100° K. is chosen in order to relax the resolution requirements to 15 bits (one part in $2^{15}$, although actual resolution provided by a 16-bit DAC is one part in $2^{16}$). That is accomplished by the temperature control DAC 64 which converts the digital temperature set point to a voltage with a resolution of one part in $2^N$, where N is equal to 16, as in the case of the wavelength set point. The output voltage of the DAC 64 provides power to the heater 16 through the sensor diode 18, and noninverting and inverting amplifiers 70 and 72. The sensor diode 18 is mounted in thermal contact with the TDL and heater, as noted hereinbefore. Biasing the sensor diode is achieved with a floating 10 μa constant current source 74 connected at one terminal to the output of the DAC 64 through a resistor $R_5$ and at the other terminal to the input terminal of the noninverting amplifier 70 which amplifies only the difference between the set point voltage (less a constant drop across the bias source 74) and the voltage drop across the sensor diode 18. This difference amplified as an error signal by the amplifier 70 is then applied to the inverting amplifier 72 which provides heating current to the heater 16. For example, if the temperature should increase, the voltage drop across the sensor diode will decrease, thereby decreasing the negative voltage at the input of the amplifier 70. Conversely, if the temperature should drop, the voltage drop across the diode 18 will increase, thereby increasing the negative input to the amplifier 70. This then increases the output of the inverting amplifier 72 to drive more current through the heater 16.

The output of the DAC 64 is used to inject a current into the set-point node 76 between resistors $R_5$, $R_6$ and $R_7$. The resistor $R_8$ and Zener diode $D_2$ provide a constant voltage to the voltage dividing network $R_6$ and $R_7$. That provides a reference voltage to the constant current source 74, and to the sensor diode 18 such that at 0 volts output from the DAC 64, the set point at the junction is 1.0695 VDC. At full scale output from the DAC 64 of 2.5 VDC, the set point is 1.1334 VDC. The resolution of the DAC is one part in $2^{16}$, so the least significant increment is about 6.36 mK. The stability of the temperature set point and the control loop is, of course, more important than resolution. The stability of the DAC 64 is about 8 parts per million per degree centigrade. This corresponds to a TDL temperature drift of only about 0.2 mK per degree centigrade change in the ambient temperature, which is quite adequate for stratospheric spectrometer measurements.

Any changes in the temperature of the TDL will also occur in the sensor diode 18 and will cause a change in the current through it. The amplifier 70 will then respond to this change and provide an error voltage to restore the temperature to the level set by the digital set point in the DAC 64, as described above. This digital set point may be changed at regular intervals while scanning through the range from 36° to 40° K. Consequently, the DAC 64 may be provided without an input register, in which case each set point is stored for the desired interval in the output buffer register of the PPI 36. It is otherwise the same as the DAC 62.

Figure 3:
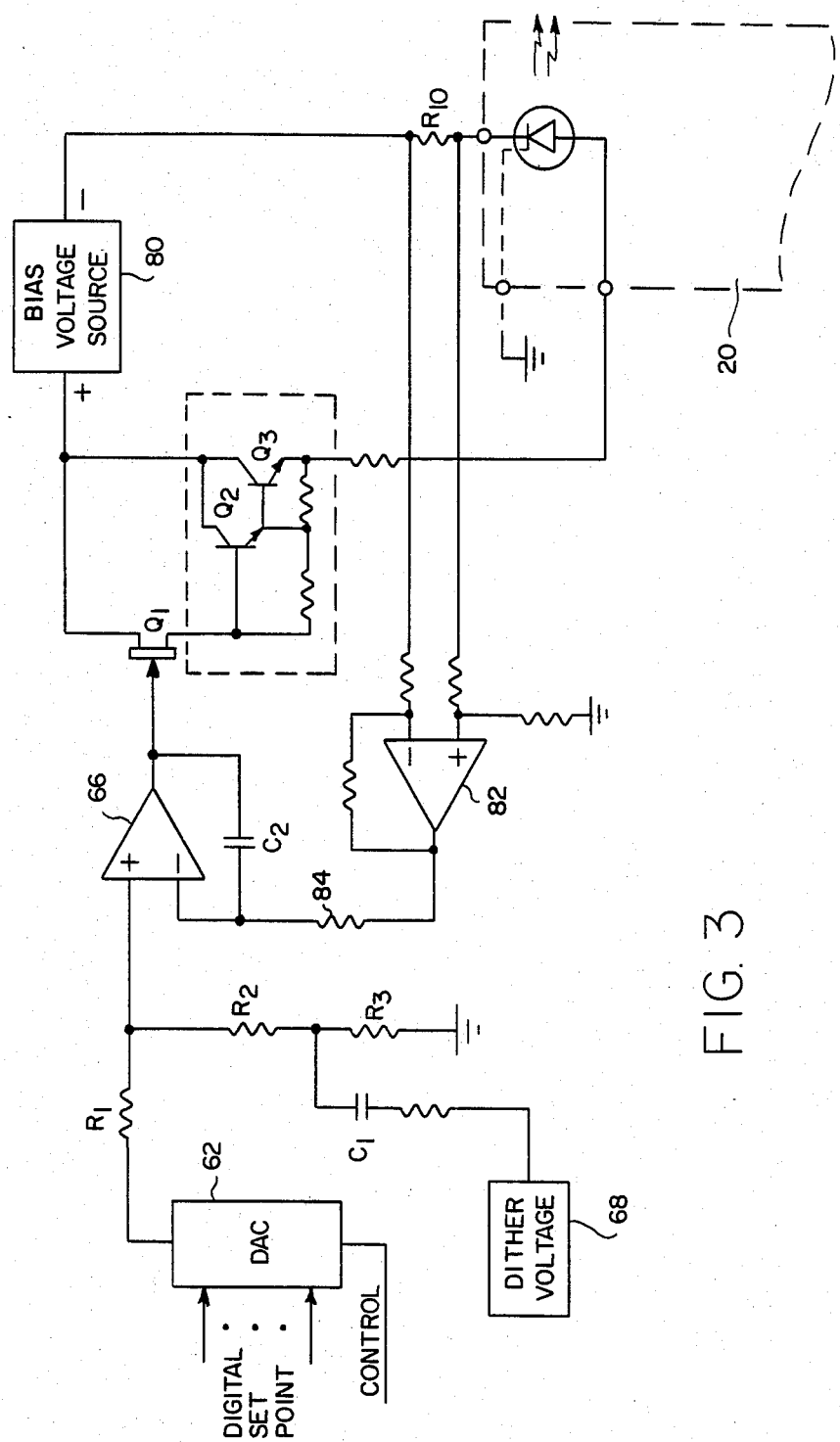
FIG. 3 is a circuit diagram for a preferred implementation of the current controller in FIG. 2.

The arrangement illustrated in FIG. 2 for current control contemplates that although the TDL is thermally coupled to the cold finger 20, such as through its cathode, it is electrically isolated. This would require an electrical insulator between the TDL and the cold finger, which would in turn impede the rate at which the TDL may be tuned by programming the cold finger temperature. It would be preferable to ground the cathode of the TDL directly to the cold finger 20, and to control its current by the FET through Darlington transistors $Q_2$ and $Q_3$, as shown in FIG. 3. These Darlington transistors are available in an integrated form (2N6059). The FET thus continues to function as the current control device, in response to the output of the amplifier 66, but the actual current from an isolated bias voltage source 80 is now through the Darlington transistors.

A current sensing resistor $R_{10}$ in series between the grounded cathode of the TDL and the voltage source 80 provides an output voltage proportional to the TDL current. This voltage is amplified and inverted by a differential input amplifier 82 coupled to the inverting input of the amplifier 66 as a feedback voltage by a resistor 84. A capacitor $C_2$ between the output of the amplifier 66 and its negative feedback input is provided to roll off higher frequency response for a more stable control of the TDL current. It should be noted that the temperature set point is stored in the DAC 64 for a significant period while the TDL is fine tuned by control of its current.

In operation, all commands and data go through the receiver to the microprocessor 28 where they are decoded. Initial parameters are stored in the EPROM 34 in the form of Hexidecimal Code and loaded into the RAM 32 with a single command. Changes in these parameters are accomplished in the RAM by a substitute memory command from the ground. Once these parameters are at the desired levels, commands to activate the settings are sent. The commands instruct the microprocessor 28 to output the address and data information to their respective ports. In a ground based system, this is analogous to dialing in, for example, a TDL current with thumbwheel switches and then pressing a button to activate the set current through the TDL.

All commands are considered as tasks by the microprocessor, which polls the tasks one at a time. If no flag is set for a given task, then the flag of the next task is tested. If that task's flag is set, the microprocessor jumps to the routine for that task in a branch table, completes the task, and clears the flag, or sets a reentrant flag, and returns to the polling routine. Then, the next task is polled and so on up to 64 tasks. If a command is received during this time, it will not be executed until the associated task is polled. The duration of any task is such that it will be completed in less than 100 milliseconds.

The measurement data readings and TDL scan increments occur at a rate determined by the timer and interrupt unit 60. For the stratospheric measurement application, this cycle time is programmed to be 125 ms. Immediately the microprocessor stops the polling process, reads the data, outputs a TDL current set point and performs several housekeeping functions.

The measurement, status, and engineering data are stored in RAM at the time they are measured. The down link data is in a serial PCM format. Consequently, the data words must be output at a constant rate bit by bit. Here again the timer 60 is used to generate a 128 Hz word rate clock and a 2048 Hz bit rate clock. The data words are then read from RAM in proper sequence and shifted through the down link to the ground station 12.

The ground station utilizes another microprocessor to format the data and commands. The 125 ms data samples are averaged on the ground to obtain integration times in excess of the basic rate. Engineering data, such as temperatures, voltages and tracking information are displayed on a terminal. Hard copy is obtained from a printer, and analog strip chart recordings are available from DAC's in the ground support equipment as well.

Science data is output to another computer for data number to engineering unit conversion and graphical display and analysis of such function measurements.

All the electronics of the TDL control 22, TDL monitor and multiplexer 42 and general control 58, are located in a separate shielded assembly. Communication between the microprocessor 28 and these shielded units goes through programmable peripheral interfaces. These interface devices can be software programmed to perform input, output or a combination of both. Since the DAC's (62 and 64) are 16 bit devices, it is convenient to use a separate interface for each, such as an Intel 8255A which has ports A and B used to set the high and low bytes respectively with a Load H and L (High and Low registers) direct instruction. Port C, which has individual bit set and reset capability, is used for various control functions such as strobing the data into the DAC's. A useful feature of the chip is the provision for reading the data stored in the output port latches. Thus, the data can be read and down linked for command verification.

Commands from the ground determine the mode of the TDL current control. If a scan mode is selected, the starting current, number of least significant bits (LSBs) of the DAC 62 per increment, and number of increments is also sent. The same capability exists for the decrement side of the scan. The shortest dwell time at any one level in a scan is 125 ms. The measurement data is integrated on board during these 125 ms periods.

Although particular embodiments of the invention have been described and illustrated herein, it is recognized that variations and equivalents may readily occur to those skilled in the art. Consequently, it is intended that the claims be interpreted to cover such variations and equivalents.

What is claimed is:

1. In a system for remote absorption spectroscopy for measurement of trace species using an infrared diode laser having emission tuned over a predetermined spectral region by control of current through said diode laser and control of the temperature of said diode laser, the combination comprising
    means for transmitting commands to and receiving data from an instrument in a remote location,
    means for transmitting commands of both current and temperature set points in digital form to said instrument,
    means in said instrument for receiving said commands and transmitting data,
    a digital data processing and control system connected to said instrument receiving and transmitting means comprising a bus and a microprocessor, tuning and interrupt means and memory connected to said bus for receiving, storing and calling up for use under a stored program commands and data, including set points for current and temperature control of said diode laser,
    current control means coupled to said bus by a peripheral interface means and responsive to said current set points called up by said microprocessor for establishing a stable current through said diode laser, and
    temperature control means coupled to said bus by a peripheral interface means and responsive to said temperature set point called up by said microprocessor for establishing a stable temperature of said diode.

2. In a system for remote absorption spectroscopy for measurement of trace species using a diode laser having infrared emission tuned over a predetermined spectral region by control of current through said diode laser and control of the temperature of said diode laser, the combination comprising
    means for transmitting both current and temperature setpoints in digital form to said instrument,
    current control means responsive to said current setpoints for establishing a stable and controlled current through said diode laser, said current control means comprising:
    a field effect transistor having a gate, and having drain and source electrodes connected with said diode laser for control of current through said laser in response to a voltage applied to said gate,
    a digital-to-analog converter connected to receive a current set point in digital form and an output terminal connected to apply a gate vltage to said field-effect transistor that is directly proportional to the current set point,
    an operational amplifier having a noninverting input an in inverting input to provide an output voltage directly proportional to the difference between an input signal at said noninverting input terminal and a feedback signal at said inverting input terminal, means responsive to the output of said current set-point digital-to-analog converter for applying to said noninverting input terminal of said operational amplifier a voltage directly proportional to the current set-point value, and means responsive to current through said diode laser for producing said feedback signal directly proportional to said current, and temperature control means responsive to said temperature set point, said temperature control means comprising resistive means thermally coupled to said diode laser for producing heat in response to current, said resistive means being thermally coupled to said diode laser, a current control amplifying means for providing current through said resistive means in response to a control voltage, a digital-to-analog converter connected to receive a temperature set point in digital form and an output terminal connected to apply said control voltage to said amplifying means, and temperature sensing means thermally coupled to said diode laser and electrically connected to provide a stabilizing feedback signal to said amplifying means.

3. A system as defined in claim 2 wherein said laser diode is so thermally coupled to said heating means and temperature sensing means as to be electrically grounded thereto at the cathode thereof, including in cascade with said field-effect transistor a Darlington pair of transistors connected to the output of said laser diode for control of current through said diode laser.

4. A system as defined in claim 3 wherein said laser diode is provided current by an isolated voltage source having its negative terminal connected to the cathode of said laser diode by said current sensing means and its positive terminal connected to the anode of said laser diode by said Darlington pair of transistors, and wherein said field-effect transistor has its drain connected to said positive terminal of said bias voltage source and its source electrode to the base electrode of said Darlington pair while the collector and emitter electrodes of said Darlington pair are connected to said bias voltage source and said anode of said laser diode, respectively, said Darlington pair of transistors being implemented as npn transistors.

5. A system as defined in claims 2, 3 or 4 including a microprocessor and memory connected to a bus for receiving and storing in said memory current and temperature set points, and for transferring to said digital-to-analog converters said current and temperature set points as required by a stored program in said memory for said microprocessor.

6. In a system absorption measurement of trace species using a diode laser having infrared emission tuned over a predetermined spectral region by control of current through said diode laser and control of the temperature of said diode laser, current control means responsive to said current setpoints for establishing a stable current through said diode laser, and temperature control means responsive to said temperature set point, the combination comprising, a field effect transistor having a gate, and having drain and source electrodes connected with said diode laser for control of current through said laser in response to a voltage applied to said gate, a digital-to-analog converter connected to receive a current set point in digital form and an output terminal connected to apply a gate voltage to said field-effect transistor that is directly proportional to the current set point, an operational amplifier having a noninverting input and an inverting input to provide an output voltage directly proportional to the difference between an input signal at said noninverting input terminal and a feedback signal at said inverting input terminal, means responsive to the output of said current set-point digital-to-analog converter for applying to said noninverting input terminal of said operational amplifier a voltage directly proportional to the current set-point value, means responsive to current through said diode laser for producing said feedback signal directly proportional to said current, means thermally coupled to said diode laser for producing heat in response to current, said resistive means being thermally coupled to said diode laser, a current control amplifying means for providing current through said resistive means in response to a control voltage, a digital-to-analog converter connected to receive a temperature set point in digital form and an output terminal connected to apply said control voltage to said amplifying means, and temperature sensing means thermally coupled to said diode laser and electrically connected to provide a stabilizing feedback signal to said amplifying means.

7. A system as defined in claim 6 wherein said laser diode is so thermally coupled to said heating means and temperature sensing means as to be electrically grounded thereto at the cathode thereof, including in cascade with said field-effect transistor a Darlington pair of transistors connected to the output of said laser diode for control of current through said diode laser.

8. A system as defined in claim 7 wherein said laser diode is provided current by an isolated voltage source having its negative terminal connected to the cathode of said laser diode by said current sensing means and its positive terminal connected to the anode of said laser diode by said Darlington pair of transistors, and wherein said field-effect transistor has its drain connected to said positive terminal of said bias voltage source and its source electrode to the base electrode of said Darlington pair while the collector and emitter electrodes of said Darlington pair are connected to said bias voltage source and said anode of said laser diode, respectively, said Darlington pair of transistors being implemented as npn transistors.

9. A system as defined in claims 6, 7 or 8 including a microprocessor and memory connected to a bus for receiving and storing in said memory current and temperature set points, and for transferring to said digital-to-analog converters said current and temperature set points as required by a stored program in said memory for said microprocessor.

* * * * *